(12) United States Patent
De Haan et al.

(10) Patent No.: US 9,376,364 B2
(45) Date of Patent: *Jun. 28, 2016

(54) ACID/SALT SEPARATION

(75) Inventors: André Banier De Haan, Bert (NL); Jan Van Breugel, Woudrichem (NL); Paulus Loduvicus Johannes Van Der Weide, Breda (NL); Peter Paul Jansen, Oss (NL); José María Vidal Lancis, Vilassar De Mar (ES); Agustín Cerdà Baró, Cerdanyola Valles (ES)

(73) Assignee: PURAC BIOCHEM B.V., Gorinchem (NL)

( * ) Notice: Subject to any disclaimer, the term of this patent is extended or adjusted under 35 U.S.C. 154(b) by 43 days.

This patent is subject to a terminal disclaimer.

(21) Appl. No.: 14/238,666

(22) PCT Filed: Aug. 16, 2012

(86) PCT No.: PCT/NL2012/050572
§ 371 (c)(1),
(2), (4) Date: Mar. 12, 2014

(87) PCT Pub. No.: WO2013/025105
PCT Pub. Date: Feb. 21, 2013

(65) Prior Publication Data
US 2014/0200365 A1 Jul. 17, 2014

Related U.S. Application Data

(60) Provisional application No. 61/524,353, filed on Aug. 17, 2011.

(30) Foreign Application Priority Data

Aug. 16, 2011 (EP) ..................... 11177633

(51) Int. Cl.
C07C 51/42 (2006.01)
C07C 51/02 (2006.01)
C01B 7/03 (2006.01)
C01F 5/10 (2006.01)
C07C 51/43 (2006.01)
C07D 307/68 (2006.01)
C01F 5/30 (2006.01)

(52) U.S. Cl.
CPC ............... *C07C 51/02* (2013.01); *C01B 7/035* (2013.01); *C01F 5/10* (2013.01); *C01F 5/30* (2013.01); *C07C 51/43* (2013.01); *C07D 307/68* (2013.01)

(58) Field of Classification Search
CPC ....................................... C07C 51/42
USPC ........................................ 562/593
See application file for complete search history.

(56) References Cited

U.S. PATENT DOCUMENTS

| 5,304,676 | A | 4/1994 | Hindmarsh et al. |
| 6,660,505 | B2 | 12/2003 | Staley |
| 2006/0276674 | A1* | 12/2006 | Kushiku et al. ............... 562/562 |
| 2008/0223519 | A1 | 9/2008 | Locko et al. |
| 2014/0364632 | A1 | 12/2014 | De Haan et al. |

FOREIGN PATENT DOCUMENTS

| CN | 1427813 A | 7/2003 |
| CN | 101748161 A | 6/2010 |
| GB | 793700 A | 4/1958 |
| KR | 10-2010-0122773 | 11/2010 |
| WO | WO 00/17378 A2 | 3/2000 |
| WO | 01/66508 A2 | 9/2001 |

OTHER PUBLICATIONS

U.S. Appl. No. 14/238,686, filed Jul. 28, 2014.*
U.S. Appl. No. 14/376,639, filed Aug. 5, 2014.*
Bischoff, J.L. et al., "The generation of HCl in the system $CaCl_2$-$H_2O$: Vapor liquid relations from 380-500° C.," *Geochimica et Cosmochimica Acta*, 1996, pp. 7-16, vol. 60, No. 1.
International Search Report issued in International Application No. PCT/NL2012/050572 on Nov. 13, 2012.
Written Opinion of the International Searching Authority issued in International Application No. PCT/NL2012/050572 on Nov. 13, 2012.
Dec. 22, 2014 Office Action issued in U.S. Appl. No. 14/238,633.
Nov. 13, 2012 International Search Report issued in International Application No. PCT/NL2012/050574.
Nov. 13, 2012 Written Opinion of the International Searching Authority issued in International Application No. PCT/NL2012/050574.
U.S. Appl. No. 14/238,686 in the name of André Bainier De Haan et al., filed Feb. 12, 2014.
U.S. Appl. No. 14/238,633 in the name of André Bainer De Haan et al., filed Feb. 12, 2014.
Nov. 13, 2012 International Search Report issued in International Application No. PCT/NL2012/050573.

(Continued)

*Primary Examiner* — Fereydoun G Sajjadi
*Assistant Examiner* — Sonya Wright
(74) *Attorney, Agent, or Firm* — Oliff PLC

(57) ABSTRACT

The invention provides a method for preparing a succinic acid, which method includes the steps of: providing magnesium succinate; acidifying the magnesium succinate with hydrochloric acid (HCl), thereby obtaining a solution including succinic acid and magnesium chloride ($MgCl_2$); optionally a concentration step, wherein the solution including succinic acid and $MgCl_2$ is concentrated; precipitating succinic acid from the solution including succinic acid and $MgCl_2$, thereby obtaining a succinic acid precipitate and a $MgCl_2$ solution. The addition of HCl to a magnesium salt of succinic acid and subsequent precipitation of succinic acid from the solution leads to a very efficient separation of succinic acid from a magnesium succinate solution.

17 Claims, No Drawings

(56) References Cited

OTHER PUBLICATIONS

Nov. 13, 2012 Written Opinion of the International Searching Authority issued in International Application No. PCT/NL2012/050573.

Davies, M. "The Solubilities of Dicarboxylic Acids in Benzene and Aqueous Solutions," Trans, Faraday Soc., vol. 49, (1953), pp. 1405-1410.

Shand, M.A., "The Chemistry and Technology of Magnesia," John Wiley & Sons, (200), excerpt, pp. 1-3.

Jun. 10, 2015 Office Action issued in U.S. Appl. No. 14/238,686.

May 29, 2013 International Search Report issued in International Patent Application No. PCT/EP2013/052525.

May 29, 2013 Written Opinion issued in International Patent Application No. PCT/EP2013/052525.

Feb. 22, 2016 Office Action Issued in U.S. Appl. No. 14/238,686.

Haynes, W. M. "Aqueous Solubility and Henry's Law Constants of Organic Compounds." CRC Handbook of Chemistry and Physics 96 (2011), pp. 5-164 to 5-185.

Kramer et al., "Crystallization," Encyclopedia of Separation Science, 2000, Academic Press, pp. 64-84.

Feb. 5, 2016 Office Action issued in Chinese Patent Application No. 201280045958.1.

Feb. 6, 2016 Office Action issued in Chinese Patent Application No. 201280046341.1.

Jan. 20, 2016 Office Action issued in Ukrainian Patent Application No. A 2014 02002.

Mar. 11, 2016 Office Action issued in Chinese Patent Application No. 201280039672.2.

\* cited by examiner

ACID/SALT SEPARATION

The invention is directed to a method for preparing succinic acid.

Succinic acid can be manufactured via fermentation of carbohydrates by micro-organisms. Fermentation processes wherein succinic acid is excreted by the micro-organisms will result in a decrease in the pH. Since such a decrease in pH can damage the micro-organism's metabolic process, it is common practice to add a base in the fermentation media in order to neutralize the pH. As a result, succinic acid produced in the fermentation media is typically present in the form of a succinate salt.

A disadvantage of obtaining succinic acid from a fermentation process in the form of a succinate salt is that one or more additional steps are required to separate succinic acid from the salt, i.e. convert the salt to a succinic acid and subsequently isolating succinic acid. This will typically lead to loss of succinic acid and/or succinate salt and thus to a decrease in the total fermentation and total process yield.

A further disadvantage of such steps is that these typically lead to considerable salt waste. For example, the separation steps often comprise acidulation of succinate salt using sulphuric acid, resulting in a sulphate salt as a waste product.

An example of a fermentation process wherein a succinate salt obtained in a fermentation process is subjected to a salt/acid separation in order to separate succinic acid from the salt is KR2010122773. This document describes a method for isolating and purifying succinic acid from a fermentation solution. First, a calcium succinate precipitate is obtained either by fermentation or by adding a base after fermentation to the fermented solution. Subsequently, hydrochloric acid and/or nitric acid are added to the precipitate to form crystalline succinic acid and calcium chloride.

A disadvantage of KR2010122773 is that it requires the formation of a solid succinate precipitate. This may complicate the separation of succinate from the solid biomass in the fermentation solution. Furthermore, the solid form of the succinate precipitate may complicate the subsequent acidification step. Further steps may be required to treat the succinate precipitate before it can be acidified.

Furthermore, KR2010122773 describes a step wherein the supernatant produced together with the crystalline succinic acid is treated in a hydration region at a temperature between 400 and 800° C. to produce hydrochloric acid or nitric acid and calcium hydroxide. Such a reaction is described in more detail by J. L. Bischoff ("*The generation of HCl in the system $CaCl_2-H_2O$: Vapor-liquid relations from 380-500° C.*", Geochimica et Cosmochimica Acta, Vol. 60, No. 1, p 7-17, 1996) and is conducted at a high pressure in the range of 250-800 bar. The presence of water during the reaction leads to the direct formation of $Mg(OH)_2$.

A disadvantage of the method of KR2010122773 is that it may lead to considerable salt waste. Even when treating the supernatant as described above, a significant amount of salt waste will still remain due to the conversion to calcium hydroxide being incomplete under the circumstances as described in KR2010122773.

A further disadvantage of the method of KR2010122773 is that it requires expensive high pressure equipment and high temperatures to treat the supernatant.

An object of the invention is to provide a separation step in which succinic acid is separated from a salt solution with a suitable conversion yield.

A further object of the invention is to provide a method with no or substantially no salt waste.

At least one of these objects was met by providing a method for preparing succinic acid, which method comprises the steps of providing magnesium succinate;

acidifying the magnesium succinate with hydrogen chloride (HCl), thereby obtaining a solution comprising succinic acid and magnesium chloride ($MgCl_2$);

optionally a concentration step, wherein the solution comprising succinic acid and $MgCl_2$ is concentrated;

precipitating succinic acid from the solution comprising succinic acid and $MgCl_2$, thereby obtaining a succinic acid precipitate and a $MgCl_2$ solution; and subjecting the $MgCl_2$ solution to a thermal decomposition step at temperatures of at least 300° C., thereby decomposing the $MgCl_2$ to magnesium oxide (MgO) and HCl.

The inventors found that a process based on above steps starting with a magnesium-based succinate, use of hydrogen chloride as acidulant and a thermal decomposition step to provide magnesium oxide creates a process with a very efficient isolation of succinic acid from a magnesium succinate solution, a high total process yield, an optimal mass and water balance and reduced product losses.

In particular, it was found that succinic acid could be precipitated from a magnesium-based succinate solution acidified with HCl with a very high efficiency. Without wishing to be bound by any theory, the inventors expect that the high efficiency of the precipitation is due to a particular high salting out effect of $MgCl_2$ under these circumstances caused by the specific combination of HCl, magnesium and succinic acid in the solution. Since salting out effects are generally hard to predict, the particular high salting out effect observed in the method of the invention came as a surprise to the inventors.

Thus, using the method of the invention, a succinic acid precipitate can be obtained in a high yield from a magnesium succinate solution, which solution is for example a fermentation mixture obtained in a fermentation process. Furthermore, the obtained succinic acid precipitate has a relatively high purity, since the precipitation step in the method of the invention does not result in precipitation of large amounts of compounds other than succinic acid (e.g. polysaccharides, chlorides such as $MgCl_2$ and other salts). In particular, the precipitate will comprise at least 85 wt. % succinic acid based on the dry weight of the precipitate.

Furthermore, the specific choice for HCl and magnesium succinate provides for a reduction in salt waste and/or improved overall process yield when combined with a thermal decomposition step as described above.

Preferably, the method further comprises the steps of subjecting the $MgCl_2$ solution to a thermal decomposition step at temperatures of at least 300° C., thereby decomposing the $MgCl_2$ to MgO and HCl; and optionally dissolving the HCl formed in the thermal decomposition step in water, thereby obtaining a HCl solution; and/or optionally bringing the MgO in contact with water, thereby obtaining magnesium hydroxide ($Mg(OH)_2$) which $Mg(OH)_2$ is optionally recycled for use in a fermentation process.

The advantage of these additional steps is that a method may be obtained that has no or substantially no salt waste. The HCl solution may be recycled to the acidulation step of the method of the invention. The $Mg(OH)_2$ can be recycled for use in the fermentation process.

The term "succinate" as used herein refers to the conjugate base of succinic acid ($Suc^{2-}$). Succinic acid ($H_2Suc$) can be obtained by acidifying succinate. Magnesium succinate refers to the magnesium salt of succinic acid (MgSuc).

The term "precipitating" as used herein refers to the formation of solid material starting from a fully dissolved state. Succinic acid can be precipitated in crystalline form or in amorphous form. By precipitating according to the method of the invention, succinic acid may also be purified. In case the magnesium succinate solution comprises dissolved impurities, precipitation typically separates succinic acid from such impurities.

The term "solution to be precipitated" as used herein refers to the solution that is to be subjected to precipitation. Typically, this term refers to the solution comprising succinic acid and $MgCl_2$ obtained after acidulation, optionally after this solution has been subjected to a concentration step and/or a step wherein extra $MgCl_2$ is added. However, in case of a second or further precipitation step, the term "solution to be precipitated" refers to the $MgCl_2$ solution obtained after the final/latest precipitation step, optionally after this solution has been subjected to a concentration step and/or a step wherein extra $MgCl_2$ is added. Such $MgCl_2$ solutions may still comprise succinic acid, which may be obtained by subjecting it to a second or further precipitation step.

Succinic acid has a solubility of 6.75 g/100 g water at 20° C. Since succinic acid has a solubility that is considerably lower than that of $MgCl_2$, $MgCl_2$ will not precipitate together with succinic acid from the solution in the precipitation step.

Magnesium succinate provided in the method of the invention may be obtained in a fermentation process.

Magnesium succinate may be provided in solid (e.g. crystalline) form. Alternatively, magnesium succinate may be in dissolved form, for example as part of a solution or suspension. Such a solution or suspension comprising dissolved magnesium succinate may be aqueous and may in particular be obtained in a fermentation process. An example of such a suspension may for example be a suspension comprising dissolved magnesium succinate and insoluble biomass, such as a fermentation broth. In case magnesium succinate is provided in dissolved form, the magnesium succinate solution or suspension may have a concentration of 1-700 g, preferably 100-600 g, more preferably 200-500 g magnesium succinate per liter solution or suspension. A concentration of up to 500 g magnesium succinate per liter will generally not lead to crystallisation of the magnesium succinate.

In case magnesium succinate is provided as a solution or suspension, the magnesium succinate concentration at which precipitation of succinic acid may occur upon acidulation depends on the HCl concentration. For example, when using a HCl solution with a high HCl concentration, e.g. between 20 and 30 wt %, to acidify the succinate, precipitation of succinic acid may occur at relatively low succinate concentrations, e.g. at around 1 to 10 wt % succinate. However, when using a lower HCl concentration (e.g. between 10 and 20 wt %), a higher succinate concentration (e.g. between 10 and 50 wt. %) may be required for precipitation to occur. For practical reasons, the upper limit of the magnesium succinate concentration in a magnesium succinate solution may be 20 wt. %, based on the total weight of the solution. Concentrations higher than 20 wt. % require the solution to have a temperature of at least 75° C. in order to have magnesium succinate in completely dissolved form. Such high temperatures are however not favourable for the equipment in terms of corrosion sensitivities due to the presence of HCl.

To yield as much succinic acid as possible after acidulation and precipitation, the succinate concentration going into the acidulation is preferably as high as possible. In case the magnesium succinate is provided as a solution, the upper limit of the magnesium succinate concentration is determined by the solubility of the magnesium succinate and the temperature at which the equipment is still sufficiently resistant against corrosion by HCl. In case the succinate is provided as a suspension, the stirrability of the suspension typically determines the upper limit. In case the succinate is provided as a solid cake, the solid liquid separation and resulting adhering water typically determine the upper limit. To support a high succinic acid yield after acidulation and precipitation, the HCl concentration is preferably as high as economically feasible, as introduction of extra water will dilute the system. The combination of the above mentioned input concentrations of succinate and HCl must favorably result in a situation where $MgCl_2$ remains in solution and as much succinic acid as possible precipitates during the precipitation step. The skilled person will be able to vary the two concentrations to obtain the desired result. For example, good results have been obtained using a combination of 15-25 wt. % HCl and a magnesium succinate concentration of 20-50 wt. % at 40-75° C.

In case a magnesium succinate solution or suspension is obtained from a fermentation process which does not have a sufficiently high magnesium succinate concentration, the solution may be concentrated, for example by evaporation.

In a preferred embodiment of the present invention, the magnesium succinate is obtained in a fermentation which uses a magnesium-based base for neutralisation in order to directly produce magnesium succinate, in contrast to first conducting fermentation and then adding a base to form magnesium succinate, to keep the process as simple as possible and to prevent using additional processing steps. The method of the present invention further preferably comprises a magnesium succinate fermentation at 25-60° C., wherein the succinate solution obtained when adding the base in fermentation comprises 1-30 wt. % magnesium succinate, such that the magnesium succinate as fermentation product is not directly precipitating. To have magnesium succinate directly precipitating in the fermentation broth during fermentation requires rather extreme fermentation conditions such as for example magnesium succinate concentrations above 40 wt. % or even above 50 wt. %, which are not favourable for the micro-organism, fermentation yield and/or equipment. To have magnesium succinate precipitating out from the fermentation broth after fermentation, preferably a separate precipitation step is applied. Such a precipitation step is for example a concentration step as explained above or a cooling precipitation as explained further below. Subsequently, the thus obtained precipitate may be dissolved in water to form an aqueous magnesium succinate solution or suspension.

The method of the invention further comprises an acidulation step, wherein the magnesium succinate is acidified with HCl, thereby obtaining a solution comprising succinic acid and $MgCl_2$. The inventors found that HCl is preferred as an acidifying agent over other acids, such as $H_2SO_4$. First, the use of HCl provides for an efficient precipitation, such as the advantageous salting out effect described earlier. In particular, the presence of $MgCl_2$ decreases the solubility of succinic acid, which results in a more efficient precipitation of the acid. Furthermore, the reaction of magnesium succinate with HCl results in salt with a relatively high solubility ($MgCl_2$), in particular compared to other magnesium salts including $MgSO_4$ and also compared to succinic acid itself. A high solubility of the salt obtained by acidifying is desirable, because as little of this salt as possible should precipitate in the precipitation step. The maximum concentration of succinic acid in the solution to be precipitated is therefore in part determined by the solubility of the salt obtained in the acidulation step. Thus, in case the salt has a high solubility, a high succinic acid concentration can be obtained without precipitation of the salt, which results in an efficient precipitation of succinic acid.

Acidulation is typically conducted using an excess of HCl. The excess is preferably small, such that the $MgCl_2$ solution obtained after precipitation is not highly acidic, which may not be desirable in view of further processing such a solution. For example, the excess of HCl used may be such that the resulting $MgCl_2$ solution after precipitation has a pH of 1 or higher, such as a pH of about 1.5. The skilled person knows how to calculate based on reaction stochiometrics the maximal allowable excess for such a pH of 1 or higher. To obtain a sufficiently complete acidulation, the resulting $MgCl_2$ solution preferably has a pH below 4, more preferably below 3.

HCl acidulation may be conducted by bringing magnesium succinate in contact with HCl, for example by bringing magnesium succinate (in solid form, solution or suspension) in contact with an aqueous HCl solution or by bringing a magnesium succinate solution or suspension in contact with HCl gas.

If a HCl solution is used in the acidulation step, it preferably comprises at least 5 wt. %, more preferably at least 10 wt. % and even more preferably at least 20 wt. % HCl. Such concentrations are sufficient to acidify magnesium succinate. High HCl concentrations may be desirable due to the above-mentioned salt out effect. Due to the low boiling point of HCl and the $HCl/H_2O$ azeotrope, the HCl concentration in a HCl solution will typically not be higher than 40%, in particular when using a HCl solution at atmospheric pressure. Preferably, a HCl concentration is used with a concentration of 15-25 wt. % HCl, based on the total weight of the HCl solution. Nevertheless, HCl concentrations of up to 100% may also be employed, in which case a HCl solution is typically used under increased pressure (e.g. above atmospheric pressure) and optionally low temperatures (e.g. below 20° C.).

In case HCl gas is used, HCl gas may be contacted by bringing it in contact with a succinate solution or suspension. In particular, HCl gas may be blown through the solution or suspension. In case HCl gas is used, the HCl may originate from a thermal decomposition step, such as for example described further below.

Preferably, acidification is conducted at a temperature of 75° C. or less. At higher temperatures, it becomes uneconomical to adapt equipment to the harsh conditions. In view of the freezing point of water, acidification is typically conducted at a temperature above 0° C. Temperatures above 20° C. may be preferred to avoid the use of cooling machines. Temperatures of 40° C. or more, or even 60° C. or more are even more preferred, because more magnesium succinate can be dissolved at these higher temperatures. The temperature of the magnesium succinate solution or suspension is typically determined by and corresponds with the temperature at which the acidification is conducted.

The method of the invention may comprise a concentration step, wherein the solution obtained after acidulation with HCl is concentrated. A higher concentration of succinic acid in the solution will increase the efficiency of the succinic acid precipitation. The concentration step may be conducted by evaporation. In the concentration step, 10-90% of the total amount of water present in the solution may be removed. However, preferably no $MgCl_2$ is precipitated as a result of the concentration. Therefore, the solution obtained after acidulation is preferably concentrated to a $MgCl_2$ concentration that is equal or lower to the saturation point of $MgCl_2$.

The method of the invention further comprises precipitating succinic acid from the solution obtained in the acidulation step or, if present, from the solution obtained in the above-mentioned concentration step. This step may be referred to as the (first) precipitation step. Precipitation may be conducted by any precipitation method known in the art, such as reactive precipitation or by cooling, concentrating, evaporating the solution to be precipitated or by adding an antisolvent to the solution to be precipitated.

Precipitation is preferably established by acidifying magnesium succinate with HCl. This type of precipitation may be referred to as reactive precipitation. In reactive precipitation, precipitation takes place during acidulation. Consequently, acidifying the magnesium succinate and precipitating the thus obtained succinic acid are conducted as one step. Accordingly, the method of the invention will comprise the steps of providing magnesium succinate obtained optionally in a fermentation process (as described above), and acidifying the magnesium succinate with HCl (e.g. an aqueous HCl solution), thereby obtaining a succinic acid precipitate and a $MgCl_2$ solution. It is noted that the precipitation step thus actually results in a suspension with the succinic acid precipitate present in the $MgCl_2$ solution.

Reactive precipitation can be conducted by choosing the conditions in the acidulation step such that immediate precipitation of succinic acid can occur. The skilled person will know how to establish such conditions. In particular, the magnesium succinate concentration may be chosen such that the acidulation with HCl will result in a succinic acid concentration that is higher than the saturation point of succinic acid.

The precipitation step may also be conducted by cooling the solution to be precipitated, e.g. the solution formed in the acidulation step, or, if present, the solution obtained in the concentration step. This type of precipitation may be referred to as cooling precipitation. The cooling step may require that the solution to be precipitated is first heated to a temperature at which substantially all $MgCl_2$ and succinic acid are dissolved. The solution to be precipitated may be cooled from a temperature above the nucleation temperature of succinic acid in the solution to a temperature below the nucleation temperature of succinic acid in the solution. The nucleation temperature is the highest temperature at which solids, in particular, precipitate, is formed. This temperature is i.a. dependent on the concentration of $MgCl_2$, succinic acid and the presence of other components. Therefore, it is not possible to give a single temperature value for the nucleation temperature. However, in general, the solution to be precipitated is cooled from a temperature of at least 35° C. to a temperature of less than 30° C., preferably at least 40° C. to a temperature of less than 25° C. Higher temperature differences make it possible to increase the yield of succinic acid precipitate. In case of a cooling precipitation the succinic acid concentration prior to cooling is preferably as close to the solubility as is economically feasible. The succinic acid concentration may be equal to the saturation point or up to 5 g/L, preferably up to 10 g/L, lower than the saturation point of succinic acid.

Furthermore, precipitation may be established by concentrating the solution comprising succinic acid and $MgCl_2$, preferably by evaporation. Evaporation of part of the solvent of the solution comprising succinic acid and $MgCl_2$ will result in a higher concentration of succinic acid and a stronger salting out effect, which enhances precipitation.

Furthermore, precipitation may be established by adding an antisolvent to the solution to be precipitated. Examples of antisolvents are alcohols, ethers and ketones.

Preferably, the $MgCl_2$ solution obtained after precipitation may be subjected to a second and/or further precipitation step, thereby forming additional succinic acid precipitate and a second and/or further $MgCl_2$ solution. The second or further precipitation step may be conducted to recover at least part of the succinic acid remaining in the $MgCl_2$ solution obtained in the previous precipitation step. In this case, this previous precipitation step of the invention may be referred to as the first precipitation step. The $MgCl_2$ solution obtained in the first precipitation of the method may still comprise small amounts of succinic acid. To recover at least part of this succinic acid, a second precipitation step may be conducted. Such a second precipitation step may be conducted under similar conditions as the first precipitation step, including a concentration step and/or the addition of $MgCl_2$ conducted prior to the precipitation step.

Thus, in a preferred embodiment, the method of the invention comprises a first precipitation reaction, which is a reactive precipitation step, after which the $MgCl_2$ solution obtained in this step is subjected to a cooling and/or evaporation step. The cooling and/or evaporation step are further precipitation steps, wherein additional succinic acid is precipitated and succinic acid losses and process yields are thus improved.

Prior to any precipitation step, magnesium chloride may be added to the solution to be precipitated or to the HCl solution. This solution to be precipitated may be the solution comprising the magnesium succinate in the acidulation (e.g. in case of reactive precipitation) or the solution comprising succinic acid and magnesium chloride as obtained in the acidulation step). Such added magnesium chloride may increase the salting out effect, thereby enhancing the precipitation of succinic acid.

A further important step in the method of the present invention comprises the step of subjecting the $MgCl_2$ solution to a thermal decomposition step at temperatures of at least 300° C., thereby decomposing the $MgCl_2$ to MgO and HCl.

Preferably the method of the invention further comprises:

dissolving the HCl formed in the thermal decomposition step in water, thereby obtaining a HCl solution; and bringing the MgO in contact with water, thereby obtaining $Mg(OH)_2$.

As described above, the advantage of these additional steps is that a method may be obtained that has no or substantially no salt waste.

Thermal decomposition used in the invention may be conducted by spraying the $MgCl_2$ solution into contact with a stream of hot gas. The temperature of the hot gas is equal to the temperature at which thermal decomposition is conducted, as described below.

The combination of thermal decomposition in an acid/salt separation of magnesium succinate from a fermentation process has to the applicant's knowledge not been described earlier. The inventors realised that $MgCl_2$ can be thermally decomposed by pyrohydrolysis at relative low temperatures (in contrast to for example compared to $CaCl_2$, which starts to decompose at about 800° C. or higher). This is advantageous, because the MgO formed will still have a sufficiently high reactivity that it can be effectively used in for example fermentation.

Suitable apparatuses for conducting thermal decomposition are known in the art. Thermal decomposition may be conducted using a roaster, for example a spray roaster or a fluid bed roaster. Such apparatuses can for example be obtained at SMS Siemag. The use of a spray roaster is preferred. A spray roaster has low energy costs (also compared to a fluid bed roaster), because it requires relatively low temperatures (as described below). A spray roaster was further found to produce reactive MgO particles, which are very suitable for use as a neutralizing agent in fermentation.

Preferably, thermal decomposition is conducted at a temperature of at least 300° C., which is the minimum temperature at which $MgCl_2$ decomposes. Preferably, thermal decomposition is conducted at a temperature of at least 350° C., for example 350-450° C. Due to energy costs, the temperature is preferably below 1000° C., more preferably below 800° C. For example, the temperature at which thermal decomposition is conducted may be 350-600° C. or 300-400° C. In addition, using a too high temperature for the thermal decomposition step is undesirable, because it will reduce the reactivity of the MgO formed, such that it is less suitable for use as a neutralizing agent in fermentation.

The thermal decomposition as applied in the present invention is preferably conducted at a pressure of 0.1-10 bar. The use of elevated pressure may be undesirable, because of an increased risk of corrosion due to the HCl not being able to condense. Most preferably, thermal decomposition is conducted at atmospheric pressure, in particular when using a roaster, to avoid unnecessary energy costs and the need for expensive high pressure equipment.

Magnesium oxide (MgO) is one of the products of the thermal decomposition and is typically obtained in the form of a powder. The magnesium oxide is preferably hydrated with water, e.g. by quenching the MgO with water, thereby forming a magnesium hydroxide ($Mg(OH)_2$ suspension. Such a magnesium hydroxide suspension is preferably recycled for use in the fermentation process. For example, the $Mg(OH)_2$ may be used as a neutralizing agent in a fermentation process. In this case, the $Mg(OH)_2$ may first be washed with water to remove chloride ions, typically to a content less than 1000 ppm. The presence of chloride ions is undesirable, because they may cause corrosion problems when added to a fermentation vessel. Since $Mg(OH)_2$ has a low solubility in water, such a washing step will typically not result in the loss of significant amounts of $Mg(OH)_2$. Alternatively, the $Mg(OH)_2$ is first converted to magnesium carbonate ($MgCO_3$), which is then used as a neutralizing agent in a fermentation process. A combination of these two steps may also be applied in which part of the Mg(OH)2 is washed and re-used and a second part is converted into MgCO3 and then re-used in the process. Part of the MgO may even be directly used in the fermentation.

The HCl obtained in the thermal decomposition step may be dissolved in water, thereby forming an aqueous HCl solution. Preferably, the HCl obtained in the thermal decomposition step is recycled by using it in the acidification step in the method of the invention, for example as HCl gas or as an aqueous HCl solution.

As mentioned earlier, the magnesium succinate provided in the method of the invention may be obtained in a fermentation process. In such a fermentation process a carbohydrate source is typically fermented by means of a micro-organism to form a succinic acid. Subsequently, a magnesium base is added as neutralising agent during fermentation to provide the magnesium salt of succinic acid. Examples of suitable magnesium bases are magnesium hydroxide ($Mg(OH)_2$), magnesium carbonate ($MgCO_3$) and magnesium bicarbonate ($Mg(HCO_3)_2$). The advantage of the use of $Mg(OH)_2$ as a base is that this compound can be provided by the method of the invention. The use of $MgCO_3$ may also be desirable and can be easily obtained by converting $Mg(OH)_2$ obtained in the method of the invention. Furthermore, the use of $MgCO_3$ or $Mg(OH)_2$ is desirable, because hydroxide and carbonate are not expected to have a negative effect on the salting out effect of the method of the invention (any carbonate left after neutralising may leave the solution as gaseous $CO_2$).

In one embodiment, the fermentation process may comprise a purification step, wherein the magnesium succinate obtained during fermentation is crystallised from the fermentation broth, which may then be subsequently dissolved in water to form an aqueous solution, which typically has a higher concentration of succinate than the fermentation broth. Such a purification step may have the advantage that a higher yield can be obtained in the first precipitation step due to the higher concentration of magnesium succinate.

However, as described above, the magnesium succinate preferably remains in dissolved form when the magnesium base is added as a neutralizing agent. This has the advantage that the magnesium succinate is pumpable and can be directly used in the acidulation step. Furthermore, the acidulation step is easy to control when the magnesium succinate is in dissolved form. In particular, the magnesium succinate present in the magnesium succinate solution or suspension obtained after adding the magnesium base comprises at least 95 wt. %, more preferably at least 99 wt. % of magnesium succinate in dissolved form. Small amounts of solids (up to 10 wt. %) may not yet lead to the negative effects described above. herhalen:

The crystallisation may comprise at least one of a concentration step, such as a water evaporation step, a cooling step, a seeding step, a separation step, a washing step and a re-crystallisation step. Concentration may be performed as a separate step or together with crystallisation (e.g. evaporative-crystallisation).

The invention is further illustrated by the following examples.

EXAMPLE 1

Magnesium Succinate Preparation

Magnesium hydroxide (99 g) was added to a solution of 200 g succinic acid in 888 g water at room temperature and heated up to complete dissolution (by visual observation).

EXAMPLE 2

Succinic Acid Precipitation

An amount of 333 g aqueous solution of HCl (37% wt %) was added to the magnesium succinate solution prepared in Example 1. The temperature of the thus obtained mixture was initially 62° C. The mixture was cooled to 20° C. and a precipitate was formed. During cooling, samples were taken of the solution and the precipitate of the mixture at 62, 52, 40, 31 and 20° C. The composition of the samples and the total amount of precipitate formed were determined.

The samples were taken only from the solution (for sampling, stirrer was stopped some few seconds, and after crystal settling, a sample was taken from the supernatant). Magnesium and succinic acid in solution were analyzed and expressed as g/g water. The amount of crystal produced was calculated as difference between the initial succinic acid mass and the mass of the succinic acid remaining in solution.

The results are shown in Table 1.

TABLE 1

| Temperature (° C.) | Succinic Acid concentration in the solution (wt %) | Mg concentration in the solution (%) | Amount of succinic acid (g) |
|---|---|---|---|
| 62 | 13.13 | 2.71 | 0 |
| 52 | 8.20 | 1.82 | 82 |
| 40 | 5.00 | 3.15 | 130 |
| 31 | 3.40 | 3.20 | 153 |
| 20 | 2.10 | 3.19 | 171 |

Furthermore, the amount of succinic acid in the 182 g precipitate formed during the cooling step was determined, which was 94.4 wt % corresponding to 172 g. The rest of the precipitate consisted mainly of water (4.4 wt %) and magnesium chloride. These findings correspond to a total recovery of succinic acid of over 85%.

This example shows that during precipitation, the majority of succinic acid precipitates, while substantially all magnesium ions remain in solution. It can be concluded that acidulation with HCl and subsequent crystallization results in a very efficient separation of succinic acid from the magnesium succinate solution.

EXAMPLE 3

Precipitation after Concentrating

To the magnesium succinate solution as prepared in Example 1 an aqueous solution of HCl (37 wt %) was added, thereby obtaining 500 g solution comprising 2.1 wt. % succinic acid and 12.6 wt. % $MgCl_2$ (corresponding to a $MgCl_2$ concentration of 14.8 g per 100 g water). The solution was then concentrated by water evaporation, thereby obtaining 199 g solution comprising 5.3 wt. % succinic acid and 31.7 wt. % magnesium chloride (corresponding to a $MgCl_2$ concentration of 50.2 g per 100 g water, which is close to the saturation point of $MgCl_2$ in water, which is 55 g/100 g water at 20 Celsius). The initial and final values of the solution are summarized in Table 2.

TABLE 2

| | mass (g) | concentration (wt %) | | MgCl2 ratio to water (mass based) g/100 gH2O |
|---|---|---|---|---|
| | | MgCl2 | Succinic | |
| initial | 500 | 12.6 | 2.1 | 14.8 |
| final | 199 | 31.7 | 5.3 | 50.2 |

The solution was then cooled from 115° C. to 20° C. Precipitation started at 82° C. and continued until 20° C. The precipitate was separated from the solution by filtration using a standard gravity filter. The composition of the precipitate and the solution is show in Table 3.

TABLE 3

| | Content succinic (%) | Cl⁻ (%) | Mg⁺² (%) | water (%) |
|---|---|---|---|---|
| Solution | 0.22 | 25.0 | 6.6 | — |

The succinic acid present in the filtrate was determined using high-performance liquid chromatography (HPLC) and was 0.22 wt. %. Assuming that all succinic acid not present in the filtrate would be present in the precipitate, the value of 0.22 wt. % would correspond to a succinic acid yield in the precipitate of over 90%.

The invention claimed is:

1. Method for preparing a succinic acid, comprising the steps of
providing magnesium succinate;
acidifying the magnesium succinate with hydrogen chloride (HCl), thereby obtaining a solution comprising succinic acid and magnesium chloride ($MgCl_2$);
precipitating succinic acid from the solution comprising succinic acid and $MgCl_2$, thereby obtaining a succinic acid precipitate and a $MgCl_2$ solution; and
subjecting the $MgCl_2$ solution to a thermal decomposition step at temperatures of at least 300° C., thereby decomposing the $MgCl_2$ to magnesium oxide (MgO) and HCl.

2. Method according to claim 1, further comprising
dissolving the HCl formed in the thermal decomposition step in water, thereby obtaining a HCl solution; and
bringing the MgO in contact with water, thereby obtaining magnesium hydroxide ($Mg(OH)_2$).

3. Method according to claim 1, wherein thermal decomposition is conducted using a spray roaster.

4. Method according to claim 1, wherein the thermal decomposition is conducted at a pressure of 0.1-10 bar.

5. Method according to claim 1, wherein the thermal decomposition is conducted at a temperature of 300-450° C.

6. Method according to claim 1, wherein thermal decomposition is conducted by spraying the $MgCl_2$ solution into contact with a stream of hot gas.

7. Method according to claim 1, wherein $Mg(OH)_2$ is converted to magnesium carbonate ($MgCO_3$), which is then used as a neutralizing agent in a fermentation process.

8. Method according to claim 1, wherein acidifying the magnesium succinate and precipitating succinic acid thus formed are conducted as one step.

9. Method according to claim 1, wherein the $MgCl_2$ solution is subjected to a second precipitation step to recover at least part of the succinic acid remaining in the $MgCl_2$ solution obtained in the first precipitation step.

10. Method according to claim 9, wherein the second precipitation is conducted by cooling and/or concentrating the $MgCl_2$ solution.

11. Method according to claim 9, wherein additional $MgCl_2$ is added to the $MgCl_2$ solution prior to the second precipitation.

12. Method according to claim 1, comprising a concentration step, wherein the solution comprising succinic acid and $MgCl_2$ is concentrated to a succinic acid concentration that is equal to the saturation point or up to 5 g/L, lower than the saturation point of succinic acid.

13. Method according to claim 1, wherein magnesium succinate is acidified with an HCl solution.

14. Method according to claim 1, wherein magnesium succinate is provided in dissolved form, as part of an aqueous solution or as part of an aqueous suspension obtained in a fermentation process.

15. Method according to claim 14, wherein the aqueous solution or aqueous suspension comprises at least 10 wt. %, based on the total weight of the solution or suspension and wherein the solution comprising succinic acid and $MgCl_2$ comprises at least 5 wt. %, based on the total weight of the solution comprising succinic acid.

16. Method according to claim 1, wherein the magnesium succinate is obtained in a fermentation process, which process comprises a purification step, wherein magnesium succinate is crystallized from the fermentation broth and then optionally dissolved in water to form an aqueous solution.

17. Method according to claim 1, wherein the magnesium succinate is obtained in a fermentation process in dissolved form, which process comprises a purification step, wherein succinic acid is neutralized by adding a magnesium base, during which step magnesium succinate remains in dissolved form.

\* \* \* \* \*